(12) United States Patent
Imbert

(10) Patent No.: US 6,190,364 B1
(45) Date of Patent: *Feb. 20, 2001

(54) SYRINGE TIP CAP

(75) Inventor: Claude Imbert, la Tronche (FR)

(73) Assignee: Becton, Dickinson and Company, Franklin Lakes, NJ (US)

( * ) Notice: Under 35 U.S.C. 154(b), the term of this patent shall be extended for 0 days.

This patent is subject to a terminal disclaimer.

(21) Appl. No.: 09/382,263

(22) Filed: Aug. 24, 1999

Related U.S. Application Data

(63) Continuation of application No. 08/847,840, filed on Apr. 28, 1997, now Pat. No. 6,027,482, which is a continuation of application No. 08/355,447, filed on Dec. 12, 1994, now Pat. No. 5,624,402.

(51) Int. Cl.$^7$ ............................................. A61M 5/14
(52) U.S. Cl. ............................................. 604/256; 604/111
(58) Field of Search .............................. 604/199, 111, 604/206, 240–243, 296, 533–535; 215/248, 296, 318

(56) References Cited

U.S. PATENT DOCUMENTS

| | | |
|---|---|---|
| 1,727,755 | 9/1929 | Dickinson . |
| 1,742,497 | 1/1930 | Dickinson . |
| 1,793,068 | 2/1931 | Dickinson . |
| 2,158,593 | 5/1939 | Scrimgeour . |
| 2,371,086 | 3/1945 | Watson et al. . |
| 2,677,374 * | 5/1954 | Burnside ............................ 604/199 |
| 2,755,801 | 7/1956 | Morando . |
| 2,764,978 | 10/1956 | Everett . |
| 2,811,155 | 10/1957 | Dunnican . |
| 3,491,757 | 1/1970 | Arce . |
| 4,043,334 | 8/1977 | Brown et al. . |
| 4,135,510 | 1/1979 | Assouly . |
| 4,187,848 | 2/1980 | Taylor . |
| 4,266,815 | 5/1981 | Cross . |
| 4,444,310 | 4/1984 | Odell . |
| 4,465,472 | 8/1984 | Urbaniak . |
| 4,597,758 | 7/1986 | Aalto et al. . |
| 4,636,201 | 1/1987 | Ambrose et al. . |
| 4,673,396 | 6/1987 | Urbaniak . |
| 4,676,530 | 6/1987 | Nordgren et al. . |
| 4,747,835 | 5/1988 | Sandhaus . |
| 4,774,772 | 10/1988 | Vetter et al. . |
| 4,781,701 | 11/1988 | Geprags . |
| 4,834,715 | 5/1989 | Hanifl . |
| 4,874,381 | 10/1989 | Vetter . |
| 5,009,640 | 4/1991 | Pyret et al. . |
| 5,069,670 | 12/1991 | Vetter et al. . |
| 5,100,010 | 3/1992 | Waters . |
| 5,104,379 | 4/1992 | Nakamura et al. . |
| 5,125,415 | 6/1992 | Bell . |
| 5,135,496 * | 8/1992 | Vetter et al. ............................ 604/111 |
| 5,135,513 | 8/1992 | Meyer et al. . |

(List continued on next page.)

FOREIGN PATENT DOCUMENTS

| | | |
|---|---|---|
| 0 022 576 A1 | 1/1981 | (EP) . |
| 0 462 355 A1 | 12/1991 | (EP) . |
| 0 589 379 A1 | 3/1994 | (EP) . |
| 1005876A1 | 7/2000 | (EP) . |

OTHER PUBLICATIONS

French Patent No. 387.123 dated Feb. 11, 1908.

*Primary Examiner*—Anh-Tuan T. Nguyen
(74) *Attorney, Agent, or Firm*—Allen W. Wark

(57) ABSTRACT

A tip cap is provided for positive sealing engagement with the tip of a syringe barrel. The tip cap includes an inner cap formed from an elastomeric material dimensioned for sealing engagement with the tip of the syringe barrel. The tip cap further includes an outer cap engaged with the inner cap to limit or prevent both axial movement and rotational movement therebetween. The outer cap includes an array of threads for threaded engagement with a luer collar. The luer collar may be a separate component mountable to a syringe barrel or an integral part of the syringe barrel.

16 Claims, 6 Drawing Sheets

U.S. PATENT DOCUMENTS

| | | |
|---|---|---|
| 5,184,742 | 2/1993 | DeCaprio et al. . |
| 5,320,603 | 6/1994 | Vetter et al. ............................ 604/82 |
| 5,403,288 | 4/1995 | Stanners . |
| 5,405,340 | 4/1995 | Fageol et al. . |
| 5,437,650 | 8/1995 | Larkin et al. . |
| 5,785,691 | 7/1998 | Vetter et al. .......................... 604/187 |
| 5,833,653 | 11/1998 | Vetter et al. . |
| 5,989,227 | 11/1999 | Vetter et al. ..................... 604/256 X |

\* cited by examiner

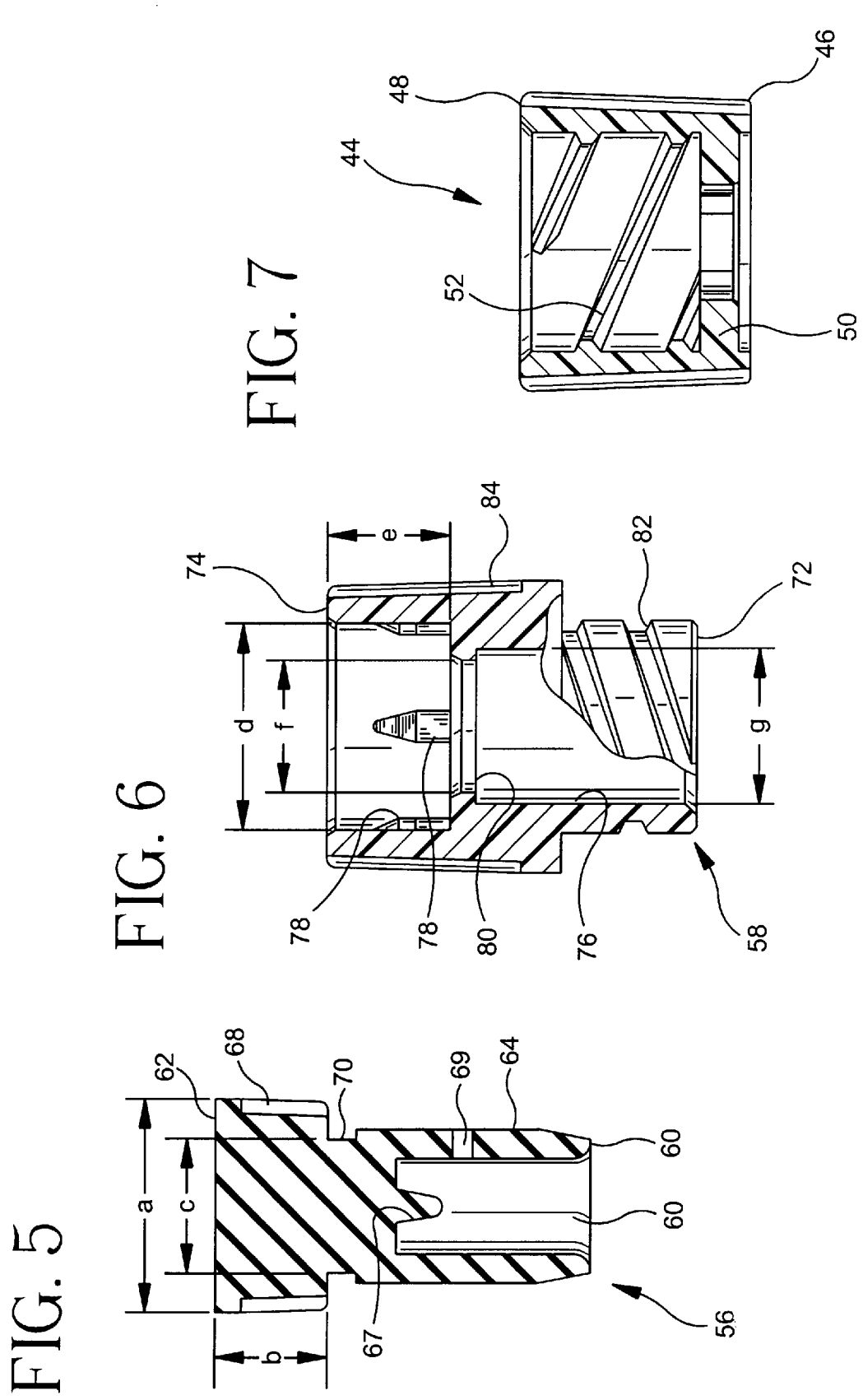

SYRINGE TIP CAP

CROSS REFERENCE TO RELATED APPLICATIONS

This application is a continuation of application Ser. No. 08/847,840, filed Apr. 28, 1997 now U.S. Pat. No. 6,027,482, which is a application Ser. No. 08/355,447, filed Dec. 12, 1994, U.S. Pat. No. 5,624,402.

FIELD OF THE INVENTION

The subject invention relates to a tip cap for securely sealing the tip of a hypodermic syringe barrel.

DESCRIPTION OF THE PRIOR ART

The prior art hypodermic syringe includes a barrel having an open proximal end and an opposed distal. A cylindrical wall extends between the ends and defines a fluid-receiving chamber. An elongate tip projects from the distal end of the prior art syringe barrel and includes a narrow passage which communicates with the fluid-receiving chamber of the barrel. A plunger may be inserted into the open proximal end of the prior art syringe barrel for sliding fluid-tight engagement with the cylindrical chamber wall. Sliding movement of the plunger in a distal direction urges fluid in the chamber through the passage in the tip. Conversely, sliding movement of the plunger in a proximal direction draws fluid through the passage in the tip and into the chamber of the prior art syringe barrel.

Prior art syringe barrels typically are made of plastic or glass. Glass exhibits lower gas transmissivity than plastic. Thus, glass syringe barrels are used for medications that are particularly susceptible to interaction with ambient gases. Glass syringe barrels also are preferably used for medications that are pre-filled into the syringe barrel and stored for a considerable period of time prior to use.

The prior art hypodermic syringe further includes a needle assembly with a needle cannula having a proximal end, a pointed distal end and a lumen extending axially therethrough. The prior art needle assembly also includes a hub which is engageable with mounting means on the syringe barrel for selectively placing the lumen of the needle cannula in fluid communication with the passage through the tip of the syringe barrel. One prior art mounting means includes a luer collar disposed in spaced concentric relationship around the tip of the syringe barrel. The luer collar includes an array of threads for threaded engagement with corresponding structure on the hub of the needle. For example, the luer collar may include an array of internal threads which are engageable with projections extending outwardly from the hub of the needle cannula. Prior art syringe barrels formed from plastic may have the luer collar unitarily molded therewith. However, glass syringe barrels cannot be formed with a unitary luer collar. Thus, glass syringe barrels and some plastic syringe barrels may have a separately formed luer collar securely mounted to the tip of the syringe barrel. The luer collar may rely upon a slip fit interengagement, a snap fit or other such secure mounting engagement around the tip of the syringe barrel.

Medications that are pre-filled into a syringe barrel must be sealed to prevent contamination or loss of the medication. Seals also prevent health care workers from being needlessly exposed to medications. The prior art has included stoppers mounted over the tip at the distal end of the syringe barrel to prevent leakage and to avoid contamination of the medication. Prior art tip caps have been formed from elastomeric material frictionally and/or resiliently retained in engagement with the tip of the prior art syringe barrel. The prior art tip cap may be removed from the syringe tip shortly prior to usage of the hypodermic syringe. The hub of the needle assembly may then be securely engaged with the luer collar or other mounting means adjacent the exposed tip of the syringe barrel. For example, the needle hub may be threadedly engaged within the luer collar such that the lumen of the prior art needle cannula communicates with the exposed tip of the prior art syringe barrel.

Prior art elastomeric tip caps on the ends of pre-loaded prior art syringe barrels generally perform well. However, the resiliently and/or frictionally engaged prior art tip cap may be accidentally disengaged from the prior art syringe barrel in response to inadvertent forces imposed thereon or due to dimensional changes or instability of the elastomeric seal. Additionally, the vacuum created as the prior art elastomeric tip cap is removed from the tip can lead to the loss of medication and unnecessary personal contact with medication that the tip cap is intended to avoid. Additionally, the prior art elastomeric tip cap provides no evidence of tampering or misuse of a pre-loaded hypodermic syringe.

SUMMARY OF THE INVENTION

The subject invention is directed to an effective tip cap assembly for a hypodermic syringe, and to a hypodermic syringe assembly having a more effectively sealed tip. A hypodermic syringe in accordance with the subject invention includes a barrel having a proximal end, a distal end and a chamber wall extending therebetween. The chamber wall defines a fluid-receiving chamber which may be pre-loaded with a selected dose of medication. The distal end of the syringe barrel includes a tip having a passage extending therethrough. The distal end may further include needle mounting means for selective engagement with mounting structure on a needle cannula. The mounting means may comprise a luer collar that is either unitarily formed with the syringe barrel or that is securely mounted to the syringe barrel in proximity to the tip.

The tip cap of the subject invention includes an elastomeric inner cap frictionally and/or resiliently engagement with portions of the tip for sealing the passage through the tip. The tip cap assembly further includes a substantially rigid outer cap engageable with the needle mounting means of the syringe barrel and protectively enclosing the inner cap. For example, the outer cap may include projections or threads engageable with threads of a luer collar integral with or mounted to the syringe barrel. The outer cap may be frictionally, resiliently and/or mechanically engaged with the inner cap. Thus, disengagement of the outer cap from the needle mounting means of the syringe barrel may simultaneously disengage the inner cap from the tip of the syringe barrel.

The inner cap and the outer cap may be separately manufactured and assembled to one another after manufacture. Alternatively, the inner cap and the outer cap may be integral with one another. In this regard, the inner or outer cap may define an insert in a mold cavity employing insert molding technology. Alternatively, the inner and outer caps may be formed by co-injection of appropriate materials into the mold cavity of an injection molding apparatus. Still further, the inner and outer caps may be formed respectively by sequential injection molding techniques using a single mold cavity.

The inner and outer caps may be assembled or molded together and subsequently attached to a needle mounting structure unitarily formed at the distal end of a plastic syringe barrel. Alternatively, the inner and outer caps may be assembled or formed together and then engaged with a plastic mounting collar for a glass syringe barrel. The assembled inner and outer caps and the mounting collar engaged therewith may then be securely mounted to the tip of a syringe barrel.

The subject invention may further include a tamper evident seal for connecting the outer cap to the needle mounting means of the syringe barrel. The tamper evident seal may comprise a severable label extending across the interface between the outer cap and the collar. Alternatively, a frangible spot weld may connect the outer cap to the luer collar or other such needle mounting means.

BRIEF DESCRIPTION OF THE DRAWINGS

FIG. 5 is a cross-sectional view taken along the longitudinal axis of the inner cap of the tip cap assembly.

FIG. 6 is a side elevational view, partly in section of the outer cap of the tip cap assembly.

FIG. 7 is a cross-sectional view taken along the longitudinal axis of the luer collar of the tip cap assembly.

DETAILED DESCRIPTION OF THE PREFERRED EMBODIMENT

Figure 1:
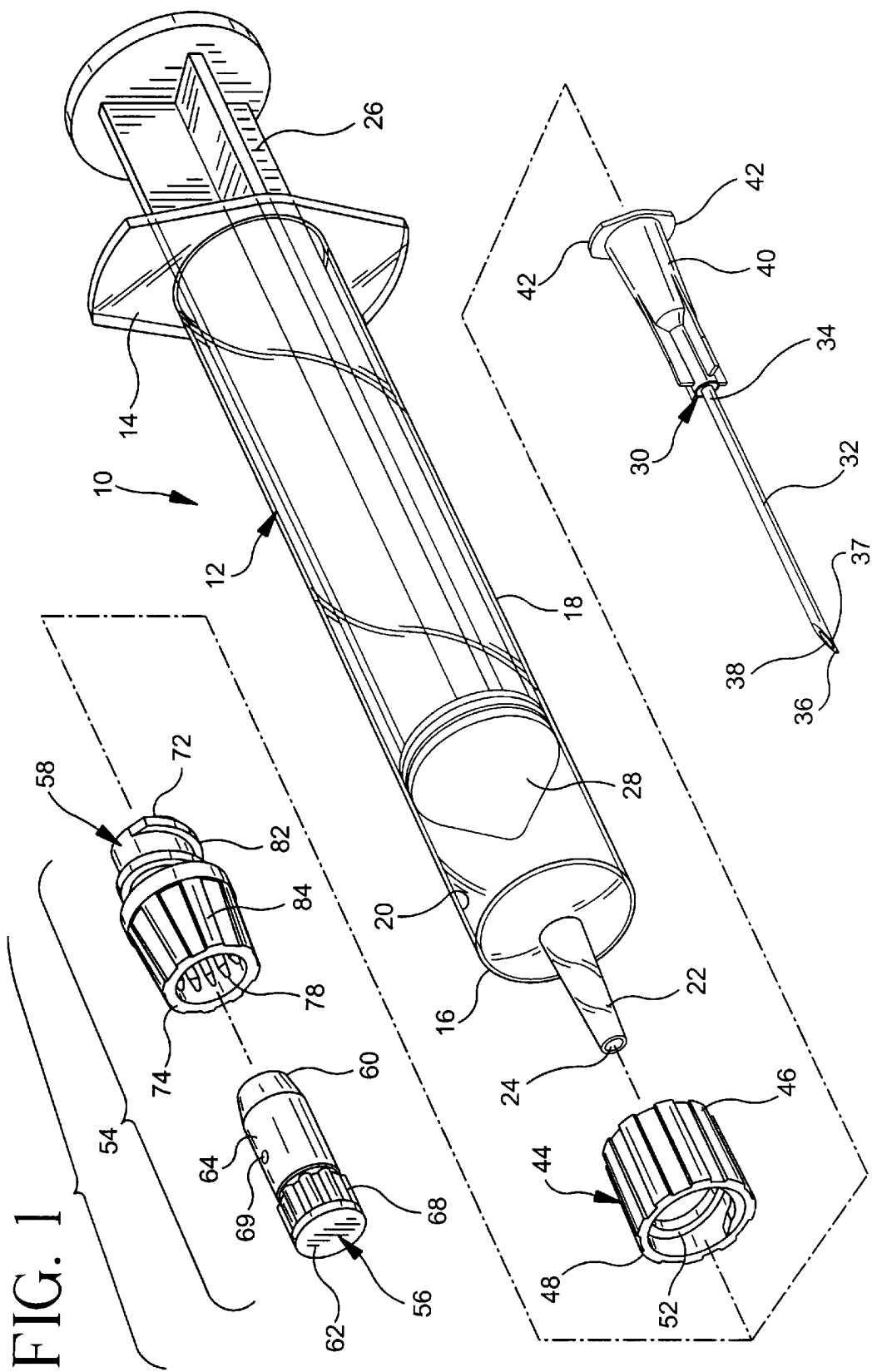
FIG. 1 is an exploded perspective view of a syringe barrel and a tip cap assembly in accordance with the subject invention.

Adverting to FIGS. 1–7, a hypodermic syringe in accordance with the subject invention is identified generally by the numeral 10. With reference to FIG. 1, hypodermic syringe 10 includes a syringe barrel 12 unitarily formed from a transparent material, such as glass or plastic. Syringe barrel 12 includes a proximal end 14, a distal end 16 and a cylindrical wall 18 extending therebetween. Cylindrical wall 18 defines a fluid-receiving chamber 20 in barrel 12. The distal end of syringe barrel 12 includes a tip 22 having a passageway 24 extending therethrough and communicating with the chamber 20. A plunger rod assembly 26 extends into proximal end 14 of syringe barrel 12, and includes a stopper 28, which is in sliding fluid-tight engagement with cylindrical wall 18 of chamber 20.

Syringe barrel 12 is used with a needle assembly 30 which includes a needle cannula 32 having a proximal end 34, a distal end 36 and a lumen 38 extending therebetween. Distal end 36 of the needle cannula preferably includes sharpened tip 37. A mounting hub 40 is securely affixed to proximal end 434 of needle cannula 32 and includes projections 42 extending therefrom for threaded engagement with a luer collar.

As noted above, syringe barrel 12 may be formed from glass, and hence does not have an integral luer collar for en(gaging mounting hub 40 of needle assembly 30. Rather, a thermoplastic luer collar 44 is provided for selective engagement over tip 22 of syringe barrel 30. More particularly, luer collar 44 is a generally hollow cylindrical structure having opposed proximal and distal ends 46 and 48. Proximal end 46 of luer collar 44 includes an array of inwardly directed projections 50 for frictionally engaging tip 22 of syringe barrel 12 and retaining luer collar 44 thereon. Distal end 48 of luer collar 44 includes an array of internal threads 52 dimensioned and pitched for threaded engagement by projections 42 of mounting hub 40 on needle assembly 30. Thus, proximal end 46 of luer collar 44 can be urged in a proximal direction over tip 22 of syringe barrel 12. Mounting projections 50 will deflect slightly and frictionally engage tip 22 to resist separation of luer collar 44 from syringe barrel 12. Mounting hub 40 may then be threadedly engaged with luer collar 44 to place lumen 38 of needle cannula 32 in communication with passage 24 through tip 22, and further in communication with chamber 20 of syringe barrel 12.

As noted above, needle assembly 30 may be maintained separate from syringe barrel 12, and may be mounted to syringe barrel 12 a short time prior to usage of hypodermic syringe 10. Syringe barrel 12 may be pre-filled with medication, and stored in its pre-filled condition prior to mounting needle assembly 30 thereto. To prevent contamination or leakage of medication stored in syringe barrel 12, a tip cap assembly is provided.

A tip cap assembly in accordance with the subject invention is identified generally by the numeral 54 in FIGS. 1–4, and includes an inner cap 56 and an outer cap 58. Inner cap 56, as shown most clearly in FIG. 5 is unitarily molded from an elastomeric material and includes opposed proximal and distal ends 60 and 62 respectively. Portions of inner cap 56 extending proximally from distal end 62 define a tip-engaging portion 64 having a cavity 66 dimensioned to tightly resilient engage tip 22 of syringe barrel 12. This preferred embodiment preferably includes a stopper 67 projecting proximally from portions of tip engaging portion 64 and defines the inner-most end of cavity 66. Stopper 67 is disposed and dimensioned to pass into passage 24 of tip 22 for further enhancing the sealing ability of inner cap 56. Inner cap 56 preferably includes a vent aperture 69 extending through tip engaging portion 64 for reducing the vacuum created as inner cap 56 is being removed from tip 22. Vent aperture 69 is disposed to be blocked by tip 22 when the inner cap 56 is fully seated. However, vent aperture 69 will permit gas communication to cavity 66 as inner cap 56 is being removed to minimize vacuum as inner cap 56 is being removed from tip 22.

Portions of inner cap 56 extending proximally from distal end 62 define a plurality of axially extending anti-rotation ribs 68 which are spaced at approximately 45° from one another about the outer circumference of inner cap 56. Anti-rotation ribs 68 define an outer diameter "a" as illustrated in FIG. 5.

Inner cap 56 further includes an annular undercut 70 extending around the outer periphery thereof at a location spaced distance "b" from distal end 62 of inner cap 56. Undercut 70 defines an outside diameter "c".

Outer cap 58, as illustrated most clearly in FIG. 6, is a generally tubular member unitarily formed from a rigid thermoplastic material. Outer cap 58 includes opposed proximal and distal ends 72 and 74 respectively and a stepped aperture 76 extending entirely therethrough. Portions of aperture 76 adjacent distal end 74 define a major inside diameter "d" which is approximately equal to the outer diameter "a" defined by anti-rotation ribs 68 adjacent distal end 62 of inner cap 56. However, portions of aperture 76 adjacent distal end 74 of outer cap 58 are characterized by inwardly extending anti-rotation ribs 78. Distal ends of ribs 78 are generally pointed for urging anti-rotation ribs 68 of inner cap 56 into positions intermediate adjacent ribs 78 during assembly of inner and outer caps 56 and 58.

Stepped aperture 76 further includes an inwardly extending annular rib 80 disposed and dimensioned to engage in annular undercut 70 in inner cap 56. More particularly, annular rib 80 is spaced a distance "e" from distal end 74, which is approximately equal to or greater than the distance "b" between undercut 70 and distal end 62 of inner cap 54. Annular rib 80 also defines an inside diameter "f" which is approximately equal to the outside diameter "c" defined by the undercut 70 in inner cap 56. Distal portions of annular rib 80 are chamfered to facilitate deflection of inner cap 56 during assembly of inner cap 56 and outer cap 58, as explained further herein.

Portions of stepped aperture 76 extending between annular rib 80 and proximal end 72 of outer cap 58 define an inside diameter "g" which is greater than the outside diameter of tip engaging portion 64 of inner cap 56, such that tip engaging portion 64 can be loosely engaged therein with room for expansion as the entire tip cap assembly is urged over tip 22, as explained further below.

Figure 4:
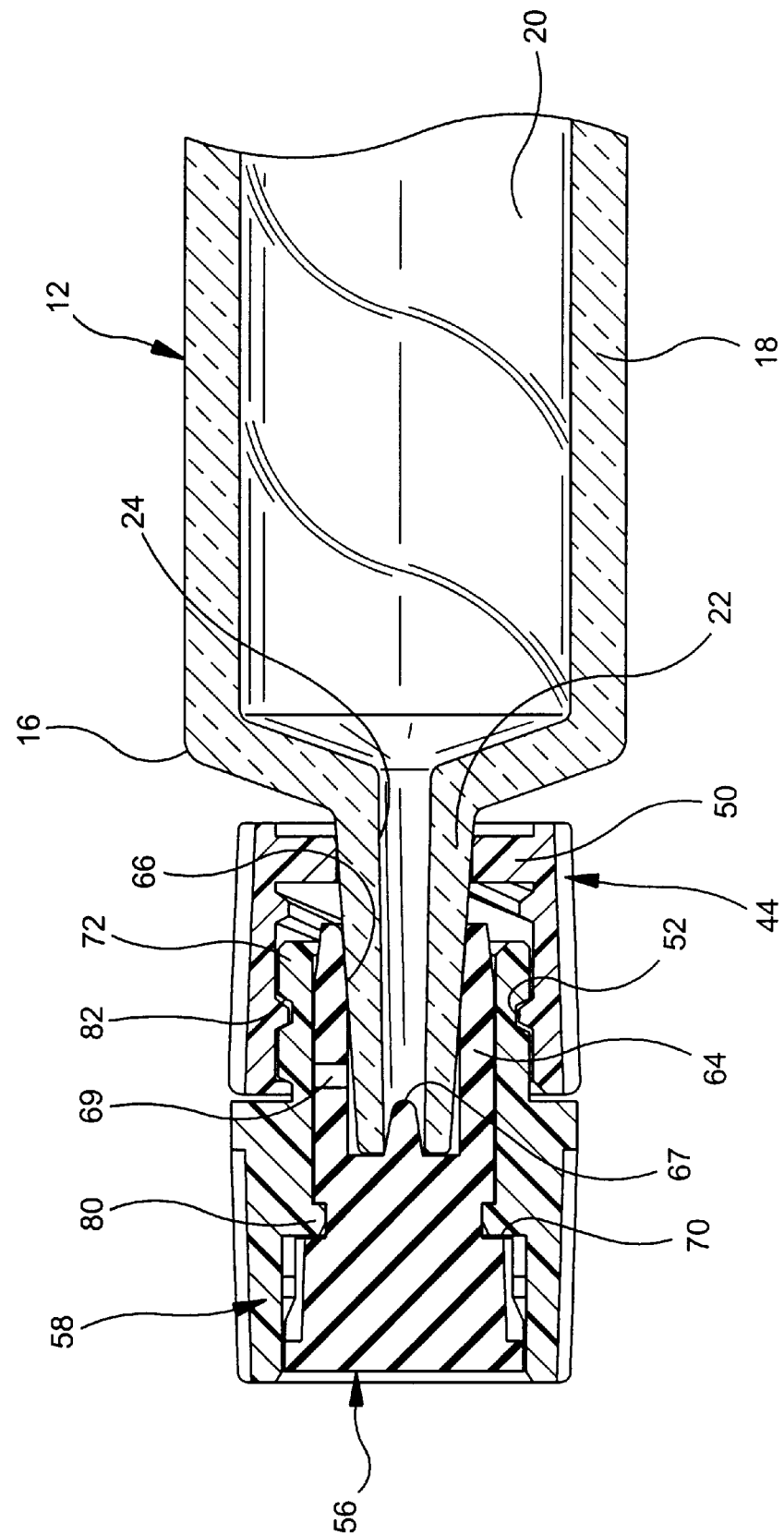
FIG. 4 is a cross-sectional view taken along line 4—4 in FIG. 3.

Exterior portions of outer cap 58 extending distally from proximal end 72 are characterized by an array of external threads 82. Threads 82 are disposed and dimensioned to threadedly engage internal threads 52 on luer collar 44 as shown in FIG. 4 above and described in greater detail below. Exterior portions of outer cap 58 extending proximally from distal end 74 are characterized by ribs 84 which are dimensioned and configured to facilitate manual gripping and rotation of outer cap 58.

Inner and outer caps 56 and 58 are assembled by urging proximal end 60 of inner cap 56 in a proximal direction into distal end 74 of outer cap 58. Tip engaging portion 64 of inner cap 56 will engage the chamfer of inwardly extending rib 80 on outer cap 58 and will be deflected inwardly. After sufficient distal movement of inner cap 56, anti-rotation ribs 68 of inner cap 56 may engage anti-rotation ribs 78 of outer cap 58. The pointed or tapered distal shape of anti-rotation ribs 78 will cause inner cap 56 to rotate slightly, such that anti-rotation ribs 68 of inner cap 56 will align respectively intermediate a pair of adjacent anti-rotation ribs 78 on outer cap 58. Further advancement of inner cap 56 into outer cap 58 will cause undercut 70 to align with annular rib 80. Inner cap 56 then will resiliently return toward an undeflected condition, such that annular rib 80 of outer cap 58 is trapped in undercut 70 to substantially prevent further axial movement between inner and outer caps 56 and 58 respectively. In this position, the interdigitation of anti-rotation ribs 68 and 78 will prevent or limit rotation between inner and outer caps 56 and 58.

Figure 2:
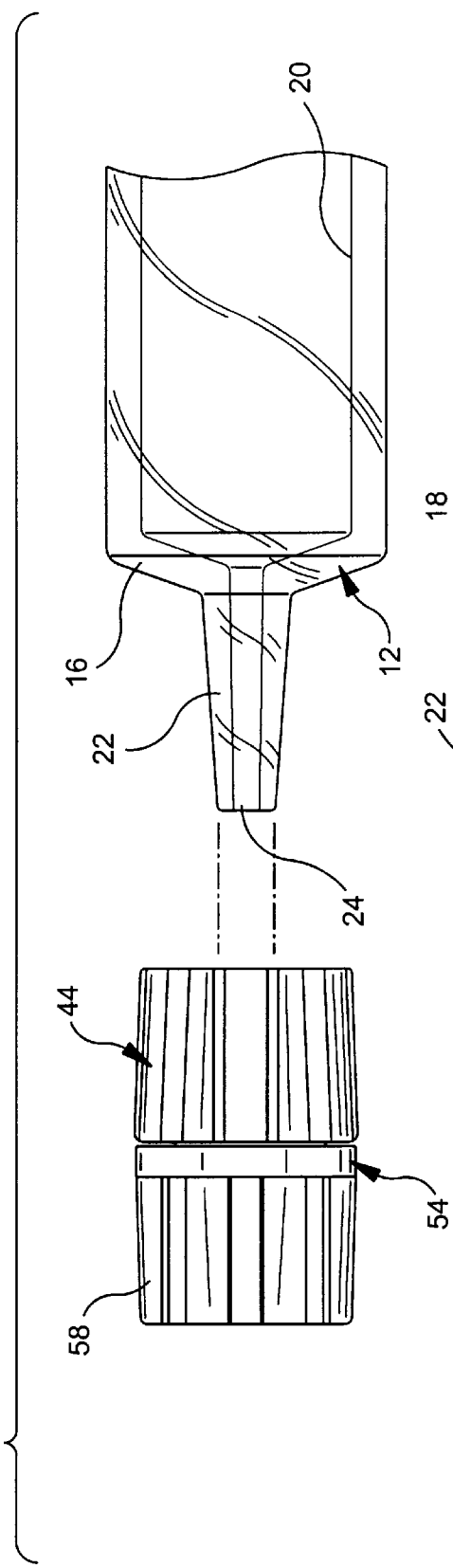
FIG. 2 is an exploded side elevational view of a syringe barrel and the tip cap assembly of FIG. 1.
Figure 3:
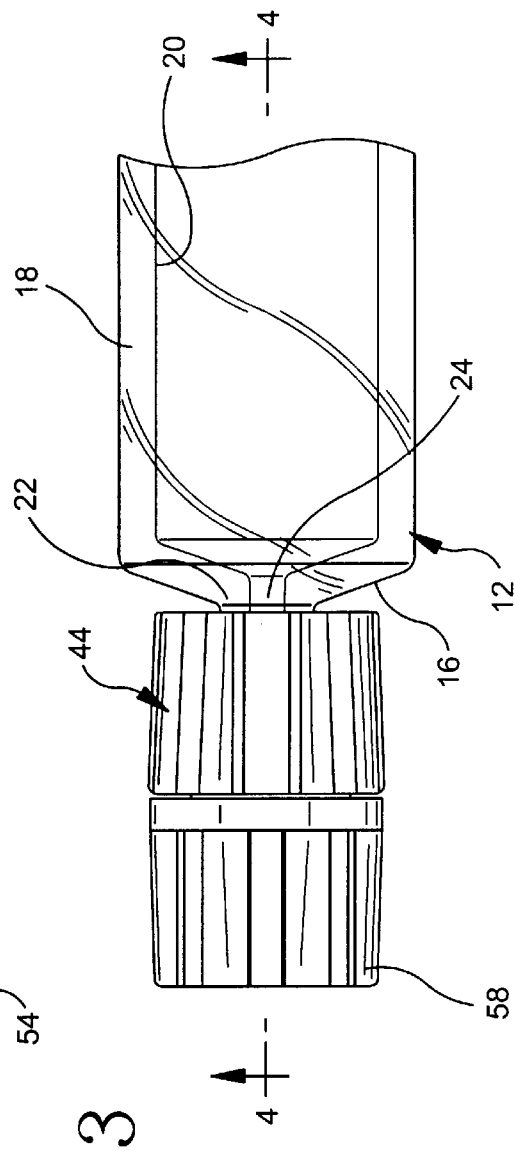
FIG. 3 is a side elevational view of the tip cap assembly and the syringe barrel of FIGS. 1 and 2 in their fully assembled condition.

Assembly 54 of inner and outer caps 56 and 58 can be threadedly engaged with luer collar 44 as shown in FIG. 2, and the threadedly engaged cap assembly 54 and luer collar 44 can be urged onto tip 22 of syringe barrel 12 as shown in FIGS. 3 and 4. Projections 50 on proximal end 46 of luer collar 44 will deflect and engage tip 22 for securely retaining luer collar 44 and the inner and outer caps 56 and 58 threadedly engaged therewith on the tip 22. Simultaneously, tip engaging portion 64 of inner cap 56 will sealingly engage tip 22. In this regard, tip engaging portion 64 will resiliently engage outer circumferential portions of tip 22, while stopper 67 will pass into and sealingly engage passage 24 through tip 22. In this fully seated position, vent aperture 69 will be blocked by tip 22.

Figure 9:
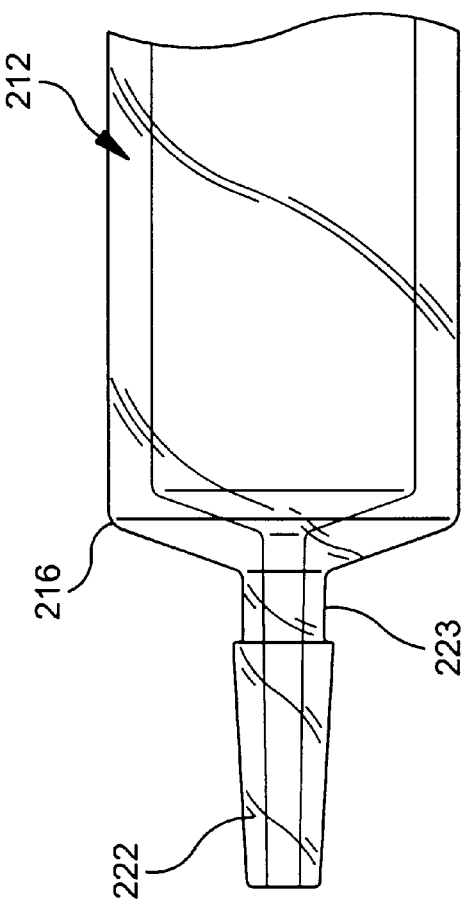
FIG. 9 is a partial side elevational view of an alternative syringe barrel of the subject invention.
Figure 10:
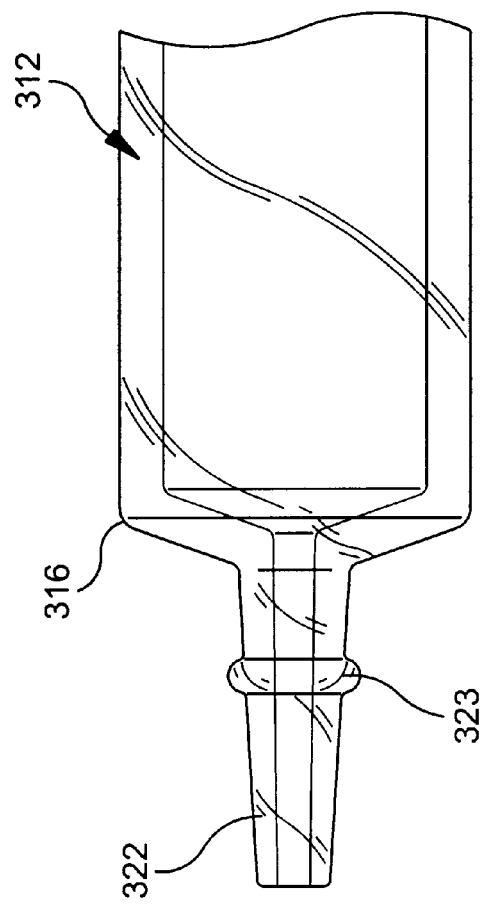
FIG. 10 is a partial side elevational view of another alternative syringe barrel of the subject invention.

FIGS. 9 and 10 illustrate alternative syringe barrels having structure for improving the engagement of projections 50 on proximal end 46 of the luer collar with the syringe barrel tip. In particular, alternative syringe barrel 212 includes distal end 216 having tip 222. Recess 226 is provided at the base of tip 222 for providing a more positive engagement with projection 50 on proximal end 46 of luer collar 44. Likewise, alternative syringe barrel 312 having distal end 316 and tip 322 includes annular rib 323 for improving the engagement of the luer collar to the barrel. During assembly, projections 50 on proximal end 46 of the luer collar must deflect and snap over annular rib 323 to secure the collar to the barrel tip. Projections 50 can be angled or chamfered to make the engagement force substantially less than the force required to pull the luer collar from the tip. Also, luer collar 44 can be attached to a syringe barrel tip through the use of other means such as adhesives.

The threaded engagement of outer cap 58 with luer collar 44 and the simultaneous engagement of outer cap 58 with inner cap 56 positively prevent inadvertent separation of inner cap 56 from its sealing engagement with tip 22. However, tip 22 of syringe barrel 12 can be accessed readily by merely rotating outer cap 58 relative to luer collar 44. Engagement of anti-rotation ribs 68 and 78 ensures that inner cap 56 will rotate with outer cap 58. Additionally, engagement of annular rib 80 of outer cap 58 with undercut 70 in inner cap 56 ensures that inner cap 56 will move axially in response to the threaded disengagement of outer cap 58 from luer collar 44.

Figure 8:
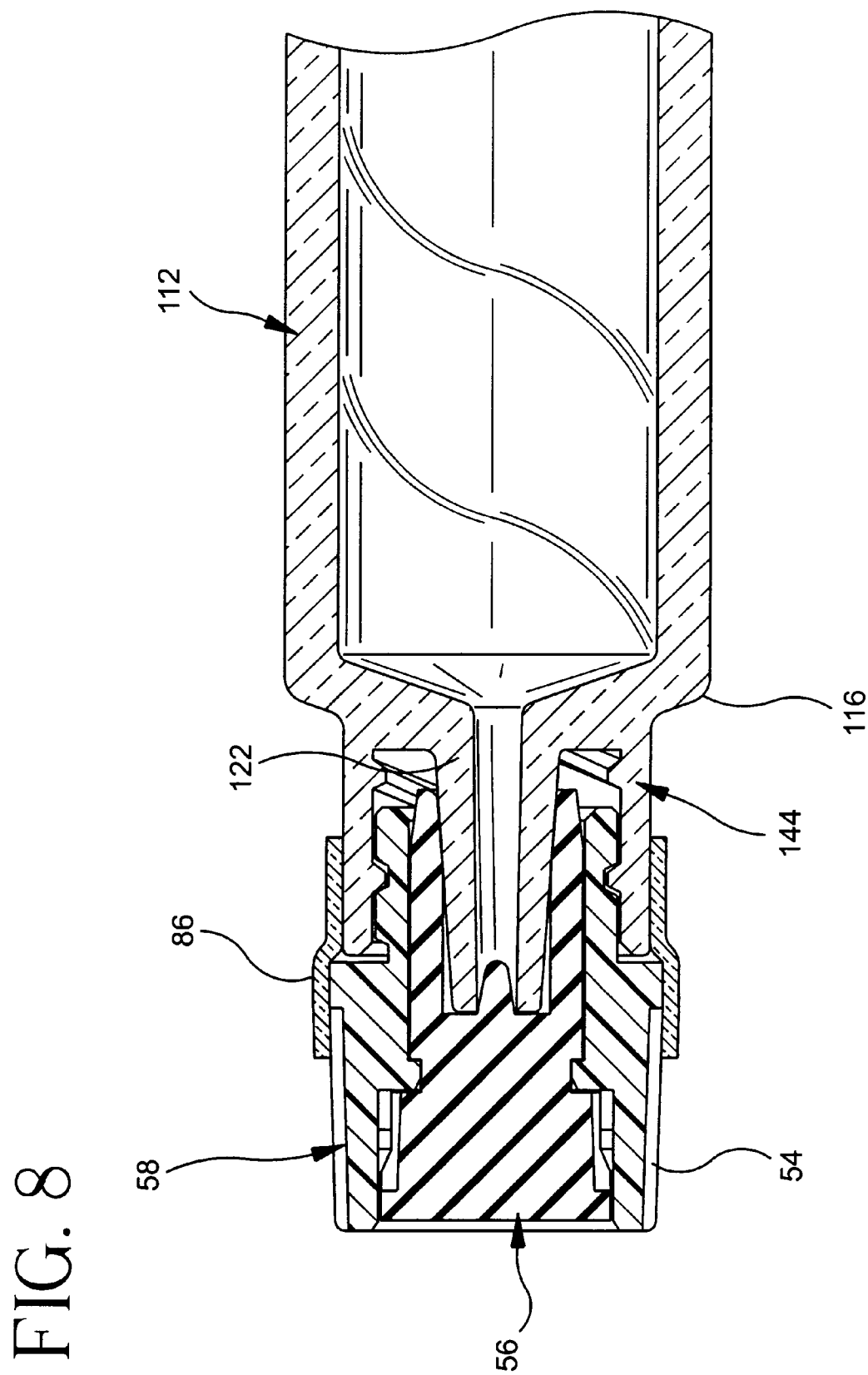
FIG. 8 is a cross-sectional view similar to FIG. 4 but showing a syringe barrel having a unitary needle mounting collar.

As illustrated in FIGS. 1–7, cap assembly 54 is threadedly engaged with a thermoplastic luer collar that is mounted to the tip of a glass syringe barrel. However, cap assembly 54 can be employed with similar advantages to a thermoplastic syringe barrel having a luer collar molded thereto. In this regard, FIG. 8 hows a thermoplastic syringe barrel 112 having a distal end 116 with a tip 122 projecting therefrom. A luer collar 144 projects unitarily from distal end 116 in spaced concentric relationship about tip 122. Cap assembly 54, as identified and described above is threadedly engaged with luer collar 144 such that elastomeric inner cap 56 sealingly engages tip 122 of syringe barrel 112. Unintended separation of inner cap 56 from tip 122 is substantially prevented by the threaded engagement of cap assembly 54 with the luer collar 144 unitarily formed with syringe barrel 112. However, tip 122 can be accessed readily by rotating outer cap 58 for threaded disengagement from luer collar 144.

As noted above, misuse of or tampering with medication pre-loaded in a syringe barrel 112 should be guarded against. To provide such tamper evidence, a frangible label 86 is adhesively applied across the interface of the threadedly engaged outer cap 58 and luer collar 144. Label 86 will serve in response to initial separation of cap assembly 54 from luer collar 44 to provide unmistakable evidence of tampering with syringe barrel 112 and the medication therein.

While the invention has been described with respect to certain preferred embodiments, it is apparent that various changes can be made without departing from the scope of the invention as defined by the appended claims. For example, the inner and outer caps need not be separate parts that are assembled after manufacture. Rather, the inner and outer caps may be simultaneously molded using injection technology or sequential injection technology. Alternatively, the inner cap or the outer cap may define an insert in an injection molding cavity in which the other of the inner and outer caps is molded.

What is claimed is:

1. A tip cap assembly for use with a hypodermic syringe barrel wherein the syringe barrel includes a distally projecting tip with a fluid passageway extending therethrough, said tip cap assembly comprising:

a collar securely engageable around a tip of a syringe barrel;

an inner cap sealingly engageable with the tip of a syringe barrel and including a cylindrically shaped side wall defining a cavity to accept the tip of a syringe barrel and a vent aperture in said side wall for preventing generation of a vacuum during removal of said tip cap assembly from the tip of a syringe barrel;

an outer cap securely disposed around said inner cap and releasably engaged with said collar; and said assembly being configured so that said inner cap sealingly engages the tip of a syringe barrel when said collar is securely engaged around the tip of a syringe barrel, and said inner cap is disengageable from the tip of a syringe barrel in response to disengagement of said outer cap from said collar.

2. The tip cap assembly of claim 1, wherein said collar includes needle mounting means for releasably engaging a needle assembly, said outer cap being releasably engageable with said needle mounting means of said collar.

3. The tip cap assembly of claim 2, wherein the needle mounting means of said collar comprises an array of threads, said outer cap comprising thread means for releasable threaded engagement with said threads of said collar.

4. The tip cap assembly of claim 1, wherein said inner and outer caps includes means for preventing relative axial movement therebetween.

5. The tip cap assembly of claim 1. wherein said inner cap is formed from an elastomeric material, and wherein said outer cap is formed from a rigid plastic material.

6. The tip cap assembly of claim 1, further comprising tamper indicator means extending between said collar and said outer cap for indicating separation of said outer cap from said collar.

7. A tip cap assembly for use with a hypodermic syringe barrel wherein the syringe barrel includes a distally projecting tip with a fluid passage extending therethrough and a luer collar concentrically surrounding the tip, and the luer collar including an array of internal threads for threadingly engaging a needle hub, said tip cap comprising:

a resilient inner cap having opposed proximal and distal ends, said proximal end defining a tip engaging portion for sealingly engaging a tip of a syringe barrel; and a rigid outer cap securely engaged around at least portions of said inner cap, said outer cap having an array of external threads threadably engageable with the threads of a luer collar so that said outer cap securely and releasably retains said inner cap in sealing engagement with the tip of a syringe barrel when said tip cap assembly is used with a syringe barrel; and wherein one of said inner and outer caps includes an annular rib, and wherein the other of said inner and outer caps comprises an annular groove engaged with said annular rib for preventing relative axial movement between said inner and outer caps.

8. The tip cap assembly of claim 1, wherein said inner and outer caps further include means for limiting relative axial movement therebetween.

9. The tip cap assembly of claim 7, wherein said inner and outer cap includes means for limiting relative rotational movement between said inner and outer caps.

10. The tip cap assembly of claim 9. wherein the means for limiting relative rotational movement comprises interdigitated axially aligned anti-rotation ribs on said inner and outer caps respectively.

11. A syringe assembly having an effectively sealed tip comprising:

a syringe barrel having a distally projecting tip with a fluid passage extending therethrough, a luer collar concentrically surrounding said tip of said syringe barrel, and said luer collar including an array of internal threads for threadingly engaging a needle hub;

a resilient inner cap having opposed proximal and distal ends, said proximal end defining a tip engaging portion sealingly engaging said tip of said syringe barrel; and a rigid outer cap securely engaged around at least portions of said inner cap, said outer cap having an array of external threads threadably engageable with the threads of said luer collar such that said outer cap securely and releasably retains said inner cap in sealing engagement with said tip of said syringe barrel; and wherein one of said inner and outer caps includes an annular rib, and wherein the other of said inner and outer caps comprises an annular groove engaged with said annular rib for preventing relative axial movement between said inner and outer caps.

12. The syringe assembly of claim 11, further comprising a frangible tamper evident seal extending between and connecting said outer cap and said luer collar.

13. A tip cap assembly for use with a hypodermic syringe barrel wherein the syringe barrel includes a distally projection tip with a fluid passage extending therethrough and a luer collar concentrically surrounding the tip, and the luer collar including an array of internal threads for threadingly engaging a needle hub, said tip cap comprising:

a resilient inner cap having opposed proximal and distal ends, said proximal end defining a tip engaging portion for sealing engaging a tip of a syringe barrel, and said proximal end of said inner cap including a cylindrically shaped side wall defining, a cavity for accepting the tip of a syringe barrel and a vent conduit in said side wall for minimizing suction during removal of said inner cap from the tip of a syringe barrel; and a rigid outer cap securely engaged around at least portions of said inner cap, said outer cap having an array of external threads threadably engageable with the threads of a luer collar so that said outer cap securely and releasably retains said inner cap in sealing engagement with the tip of a syringe barrel when said tip cap assemble is used with a syringe barrel.

14. A tip cap assembly for use with a glass syringe barrel wherein the syringe barrel includes a distally projecting tip with a fluid passage extending therethrough, said tip cap assembly comprising:

a luer collar formed from a thermoplastic material and having means for securely locking said luer collar to a tip of a syringe barrel, said luer collar having an array of internal threads in spaced concentric relationship around the tip of a syringe barrel;

an resilient inner cap having opposed proximal and distal ends, said proximal end being configured for sealingly engaging the tip of a syringe barrel, said proximal end having at least one anti-rotation rib, portions of said inner cap intermediate said proximal and distal ends defining a locking surface; and a rigid outer cap disposed in generally surrounding relationship to said inner cap, said outer cap including at least one axially extending projection engaged with said rib of said inner cap for controlling relative rotation between said inner and outer caps, said outer cap further comprising at least one surface engaged with said locking surface of said inner cap for preventing relative axial movement therebetween, and said outer cap comprising an array of external threads threadedly engaging said threads of said luer collar, said threads being disposed for urging said inner cap into tight sealing engagement with the tip of a syringe barrel in response to tightening of said outer cap to said luer collar whereby threaded disengagement of said outer cap from said luer collar disengages said inner cap from the tip of a syringe barrel.

15. The tip cap assembly of claim 14, further comprising vent means in said inner cap for minimizing vacuum during separation of said inner cap from the tip of a syringe barrel.

16. The tip cap assembly of claim 14, further comprising a frangible tamper evident seal extending between and connecting said outer cap and said luer collar.

* * * * *